United States Patent
Jain

(10) Patent No.: US 11,107,557 B1
(45) Date of Patent: Aug. 31, 2021

(54) FORCE FIELD BASED MOLECULAR STRUCTURE AND CONFORMER GENERATION

(71) Applicant: Ajay Naresh Jain, Los Altos, CA (US)

(72) Inventor: Ajay Naresh Jain, Santa Rosa, CA (US)

(*) Notice: Subject to any disclaimer, the term of this patent is extended or adjusted under 35 U.S.C. 154(b) by 805 days.

(21) Appl. No.: 15/873,679

(22) Filed: Jan. 17, 2018

Related U.S. Application Data

(60) Provisional application No. 62/453,938, filed on Feb. 2, 2017.

(51) Int. Cl.
*G01N 33/48* (2006.01)
*G01N 33/50* (2006.01)
*G16C 20/80* (2019.01)
*G16C 10/00* (2019.01)

(52) U.S. Cl.
CPC .............. *G16C 20/80* (2019.02); *G16C 10/00* (2019.02)

(58) Field of Classification Search
CPC .................................. G16C 20/80; G16C 10/00
See application file for complete search history.

(56) References Cited

PUBLICATIONS

Cleves et al. ForceGen 3D structure and conformer generation: from small lead-like molecules to macrocyclic drugs. Journal of Computer-Aided Molecular Design. vol. 31, pp. 419-439, Mar. 13, 2017.*
Chen et al. Tackling the conformational sampling of larger flexible compounds and macrocycles in pharmacology and drug discovery. Bioorganic & Medicinal Chemistry, vol. 21, pp. 7898-7920. (Year: 2013).*
MacKerell et al. All-atom empirical potential for molecular modeling and dynamics studies of proteins. Journal of Physical Chemistry B, vol. 102, pp. 3586-3616. (Year: 1998).*

* cited by examiner

*Primary Examiner* — Russell S Negin

(57) ABSTRACT

Systems and methods for molecular structure generation and conformer elaboration, in which natural physical molecular movements can be combined with a molecular force field that constrains those movements, to rapidly produce conformational variants with relatively low energy. Construction and energy minimization of initial and subsequent 3D molecular models using force field parameters, are combined with alteration of the molecular model using biophysical transformations, to generate one or more conformations thereof. The biophysical transformations each include natural physical movements of parts of the molecule, such as rotation of atoms or bonds about a selected axis in the 3D molecular model. The selected axis can define ring components, selected bonds within a macrocyclic ring, selected bonds joining substituents or other portions of the molecule, or axes or lines defining one or more geometric features of the molecular model. Once altered using biophysical transformations, the 3D molecular model can also have energy minimization performed with respect to a molecular force field model. A subset of the generated conformers can be collected, compressed from time to time, and selected for output.

18 Claims, 2 Drawing Sheets

US 11,107,557 B1

FORCE FIELD BASED MOLECULAR STRUCTURE AND CONFORMER GENERATION

TABLE OF CONTENTS

INCORPORATED DISCLOSURES
BACKGROUND
SUMMARY OF THE DISCLOSURE
BRIEF DESCRIPTION OF THE FIGURES
DETAILED DESCRIPTION
   GENERAL DISCUSSION
   TERMS AND PHRASES
   FIGURES AND TEXT
   Generation of Initial Conformational Candidates
   Generation of Conformational Variants
   Verification of Conformational Variants
   Compression of Conformational Variants
   Presentation of Conformational Variants
   Results
   ALTERNATIVE EMBODIMENTS
CLAIMS
ABSTRACT OF THE DISCLOSURE

INCORPORATED DISCLOSURES

Priority Claim

This application claims priority, to the fullest extent permitted by law, of the following documents:
   U.S. Provisional Application 62/453,938, filed Feb. 2, 2017, naming inventor Ajay Jain, titled "Force Field Based Molecular Structure and Conformer Generation".

Each of these documents is hereby incorporated by reference as if fully set forth herein.

Other Incorporated Documents

Techniques described in this Application can be used with ideas described in the preceding documents from which priority is claimed. Techniques described in this Application can also be used with ideas described in the following documents:
   An article titled "ForceGen 3D structure and conformer generation: from small lead-like molecules to macrocyclic drugs", Journal of Computer-Aided Molecular Design, ISSN 0920-654X, volume 31, number 5, pages 419-439, DOI 10.1007/s10822-017-0015-8, also enclosed as a technical appendix.

Each of these documents is hereby incorporated by reference as if fully set forth herein. Techniques described in this Application can be elaborated with detail found therein.

BACKGROUND

Field of the Disclosure

This Application generally describes techniques relating to computational chemistry, including three-dimensional (3D) molecular structure and conformation generation.

Related Art

Computational chemistry includes attempts to discern three-dimensional (3D) structure for a molecule, given the atomic components of that molecule. This might be valuable in attempting to determine whether that molecule is likely to bind to a known molecular structure, such as a biological structure. Computational chemistry is sometimes used in drug lead discovery and other fields, to assist in determining whether one or more molecules are promising candidates for biochemical testing.

One problem with known methods for generating molecular structures and conformations is that there can be many possibilities for structures corresponding to a known molecular composition, and that there can be many conformations corresponding to a known molecular structure. Even when the molecular structure is known, each conformation reasonably corresponding to that structure can take substantial time to generate, and there can be a very large number of possible conformations.

For example, known methods for discerning 3D structures of molecules, and their conformational variants, typically use pre-computed templates to construct initial 3D molecular models, such as from ring components, non-ring linkers, and substituents. In these known methods, heuristic sampling of torsions or stochastic sampling is used to adjust the pre-computed templates. These known methods can be limited in practical utility due to limitations in generality of applicability to drug-like compounds and with respect to molecular ring structures, and limitations due to lack of speed. While these known methods can be adequate with respect to simple molecules, the typically involve stochastic sampling for more complex molecules, such as those involving novel ring systems or large macrocyclic ring systems (cyclic chains larger than about eight or nine atoms). For those more complex molecules, known methods have sometimes used $10^3$-$10^5$ seconds of typical wall-clock time, even for the most effective methods. This can provide limits to their practical utility.

Each of these issues, as well as other possible considerations, might cause difficulty in aspects of computational chemistry systems and methods, particularly in those systems and methods in which molecular structure and conformer generation are performed.

SUMMARY OF THE DISCLOSURE

This Application describes systems and methods for 3D molecular structure generation and conformer elaboration. In one embodiment, natural physical molecular movements can be combined with a molecular force field that constrains those movements, to rapidly produce conformational variants with relatively low energy. Structure generation and conformer elaboration can include: (A) construction and energy minimization of an initial 3D molecular model using force field parameters, and (B) alteration of the 3D molecular model using biophysical transformations, to generate one or more conformational variants thereof. The biophysical transformations can each include natural physical movements of parts of the molecule, such as rotation of atoms or bonds about a selected axis in the 3D molecular model. The selected axis can define ring components, selected bonds within a macrocyclic ring, selected bonds joining substituents or other portions of the molecule, or axes or lines defining one or more geometric features of the molecular model. Once altered using biophysical transformations, the 3D molecular model can also have energy minimization performed with respect to a molecular force field model. A subset of the generated conformers (such as a subset with minimum energy of conformers and maximum differences between pairs of conformers) can be collected, compressed from time to time, and selected for output.

BRIEF DESCRIPTION OF THE FIGURES

In the figures, like references generally indicate similar elements, although this is not strictly required. After reading this Application, those skilled in the art would recognize that the figures are not necessarily drawn to scale for construction, nor do they necessarily specify any particular location or order of construction.

DETAILED DESCRIPTION

General Discussion

Figure 1:
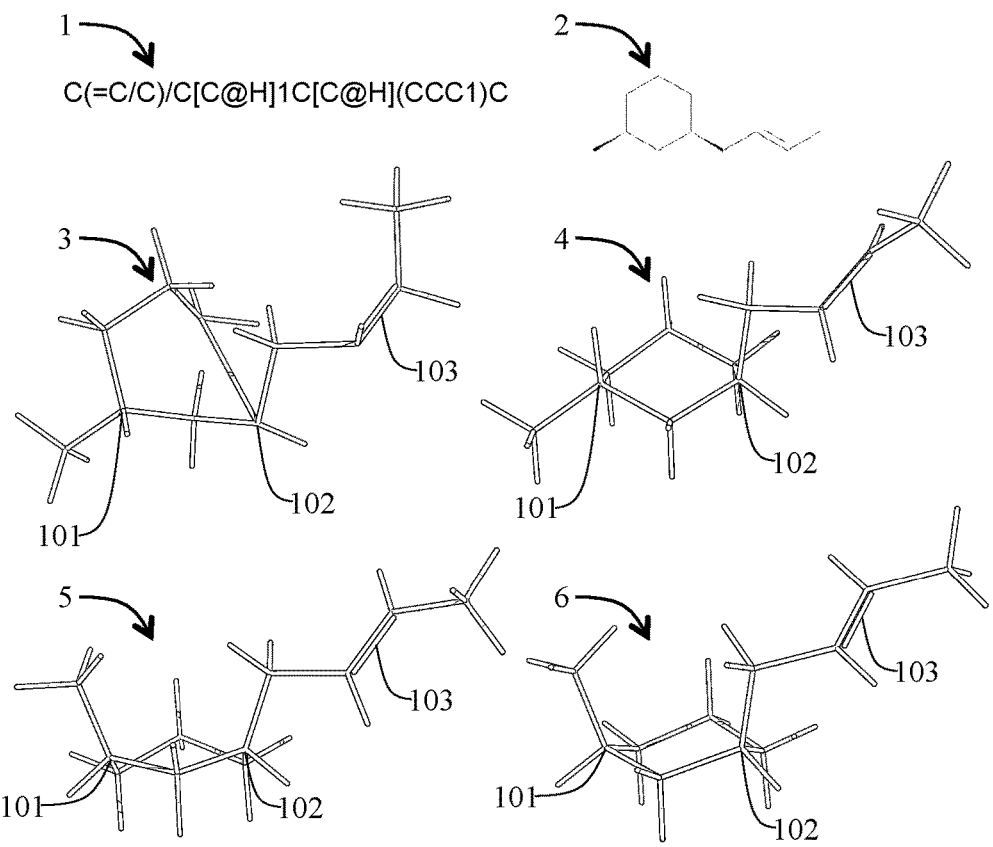
FIG. 1 shows a conceptual drawing of a first example molecular structure, including a linear structure, a 2D structure, and possible 3D structures.

Systems and methods for molecular structure generation and conformer elaboration can include a 3D model of molecular structure, a technique for altering molecular structure to generate conformational variants, a force field model of energy of conformational variants, and a technique for collecting sufficient conformational variants. Experiments with the systems and methods show that the collections of conformational variants generated thereby match physical chemistry results to a greater degree and with fewer resources than known methods.

In methods described herein, molecular structure generation can include: first, production of one or more conformational candidates, and second, generation of a set of conformational variants from the conformational candidates. The generated set of conformational variants can be compressed, such as by removing those which are insufficiently distinct, or those which have excessive relative energy, or with respect to other factors.

Production of a conformational candidate can include: initial construction of a set of three-dimensional atomic positions, energy minimization with respect to a force field with an initial set of parameters, refinement of the force field parameters, iteration of the energy minimization and force field refinement steps to provide a refined molecular structure, verification of the refined molecular structure with known configuration and energy limits, iteration of steps to provide a set of conformational candidates, and selection of one or more conformational candidates for generation of conformational variants.

Generation of a set of conformational variants can include: performing a biophysical transformation to alter the molecular model, energy minimization while maintaining the biophysical transformation in effect, further energy minimization on the altered molecular model, iteration of steps to provide a conformational variant, compression of the set of conformational variants with respect to differences and energy limits, and selection of conformational variants for presentation.

Terms and Phrases

The phrase "biophysical transformation" (and similar phrases) generally refers to an alteration of a molecular model that is representative of a transformation that can occur in the physical world. For example, and without limitation, this phrase can refer to altering the positions of a subset of atoms with respect to an atomic bond. For another example, and without limitation, this phrase can refer to altering the position of a subset of atoms so that their positions with respect to other atoms are changed relative to a geometric feature derived from the positions and topology of the other atoms.

Figures and Text

A method of operation can include steps as described herein. While the steps are shown and described in a linear order, in the context of the invention, there is no particular requirement for any such limitation. Except where explicitly stated, there is no particular requirement for the steps to be encountered or performed linearly, or in any particular order or by any particular device. For example and without limitation, the steps can be encountered or performed in parallel, in a pipelined manner.

Although this Application primarily describes one preferred technique for generating the conformational candidate, in the context of the invention, there is no particular requirement for any such limitation. Other techniques for generating the conformational candidate would be workable, and could be incorporated into the method along with the techniques for generating conformational variants. The conformational candidate could even be received from another system or program routine.

Generation of Initial Conformational Candidates

Initial Construction of 3D Atomic Positions

FIG. 1 shows a conceptual drawing of a first example molecular structure, including a linear structure, a 2D structure, and possible 3D structures. This example molecular structure is di-substituted cyclohexane with two chiral carbon atoms and a trans double-bond. FIG. 1 shows the description of chiral di-substituted hexane in a SMILES string notation 1. FIG. 1 also shows a two-dimensional (2D) rendering 2 of the molecule, as an optional second description or representation.

Given the input molecular structure, a method can produce (preferably) one or (optionally) more than one conformational candidate. To produce a conformational candidate the method can note atom chirality, such as at 101 and 102, and carbon-carbon double-bond configurations, such as at 103. The method can then assign initial atomic positions 3, such as recursively, that is, each atom is assigned a position in response to earlier assignments of atomic positions 3.

For example, the initial atomic positions 3 can be selected one after another using approximations. These approximations can include: (1) modeling each heavy atom as a tetrahedron without respect to its hybridization state, (2) modeling each atomic bond with an approximate bond length rather than attempting to select a more exact bond length, (3) modeling connections between distinct atomic tetrahedral using anti rather than gauche conformational configurations. For another example, the initial atomic positions 3 can include a standard alkane C—H bond length for bonds between hydrogen and any heavy atom, and a standard alkane C—C bond length for all other bonds.

This can have the effect that molecules with ring structures can be assigned atomic positions that are not near-perfect, but instead have a relatively small number of poorly selected bond lengths and geometries. In later iterations of assignment of initial estimated positions, as described herein, the choice of torsional angle and assignment of atoms within individual tetrahedra can be varied, with the effect that those further iterations can achieve relative diversity of selection of initial position assignment.

For example, the initial assignment of atomic positions 3 (shown in FIG. 1) is mostly reasonable, except for the atoms that close the hexane ring, and the atoms that are not supposed to be tetrahedral.

Energy Minimization Using Force Field Model

Having assigned initial atomic positions 3 (shown in FIG. 1), the method can minimize the energy of the molecular structure using a force field model. In one embodiment, the can assign an initial set of parameters to a force field to be applied to the 3D model of atomic positions, and perform energy minimization with respect to a relatively simple variant force field.

For example, the method can initially assign atomic partial charges uniformly to −0.1 (electron charge), and can construct an initial force field, in response to an initial set of parameters. The first set of parameters can include at least some of: terms to enforce bond lengths, bond angles, stretch-bend interactions, torsional configurations, out-of-plane bending, Van der Waals interactions, and electrostatic interactions. The method can perform energy minimization with respect to a force field responsive to this initial assignment, with the effect of generating an initial refinement 4 (shown in FIG. 1) of the molecular structure.

For example, the method can perform the energy minimization in Cartesian space ($R^3$), using a quasi-Newton minimization technique such as the Broyden-Fletcher-Goldfarb-Shanno (BFGS) algorithm, or a variant thereof. The BFGS algorithm is known in the art of minimization techniques, and is described in part at Press, W. H., Flannery, B. P. and Teukolsky, S. A., 1986. WT Vetterling Numerical Recipes in C: The Art of Scientific Computing. Cambridge University Press, Chapter 10, hereby incorporated by reference. Other optimization techniques are also applicable. However, in preferred embodiments, other optimization techniques preferably exclude stochastic methods, and preferably make use of methods that can take advantage of derivatives, such as a first derivative, of the force field function.

Energy Minimization Using Refined Force Field Models

After initial refinement 4 (shown in FIG. 1), the method can further refine the force field, such as by using further terms in response to additional parameters. For example, these additional parameters can include terms to enforce desired chirality at tetrahedral centers. The method can perform energy minimization with respect to a force field responsive to these further terms.

The method can still further refine the force field, such as by using still further terms in in response to additional parameters. For example, these additional parameters can include (1) terms in response to other torsional terms, (2) relatively strongly weighted torsional terms in response to desired double-bond geometry, and possibly other terms. The method can perform energy minimization with respect to a force field responsive to these still further terms.

The method can continue to further refine the force field, such as by (1) removing terms for special enforcement of configurational requirements, (2) assigning more realistic partial charges, such as standard partial charges, and possibly other force field terms. The method can perform energy minimization with respect to a force field responsive to this continued refinement of terms. The method can continue to refine terms for the force field, and continue to perform energy minimization, until a substantially final refinement of the force field and energy minimization are performed.

As described herein, energy minimization with respect to the initial force field can produce an improved molecular structure 4 (shown in FIG. 1) (using terms for bond length, bond angle, and electrostatic repulsion). However, in the molecular structure 4 (shown in FIG. 1) the chirality of one of the methyl substituents is not correct, and the double bond is out-of-plane. Energy minimization with respect to the refined force field can produce a further improved molecular structure 5 (shown in FIG. 1) (using further terms for tetrahedral chirality). Energy minimization with respect to a still-further improved substantially final molecular structure 6 (shown in FIG. 1) (using terms for cis/trans chirality, torsion, and realistic partial charges, and without special chiral enforcement terms), in response to successive refinement of parameters of the force field model.

The force field parameters can represent the MMFF94sf force field (as further described in the Technical Appendix, hereby incorporated by reference), or a variant thereof, with energy minimization seeking the local minima of the force field. More detailed force field parameters can represent dipole/quadrupole and other multipole electromagnetic effects, quantum mechanical effects, temperature effects, vibration effects, and other empirical or semi-empirical effects.

For example, energy minimization for pharmaceuticals and related molecules typically assumes a solution pH of about 7.4, but can assume a solution pH of about 4.0 for HIV-related molecules, and can assume other solution pH values in other contexts. For another example, energy minimization for pharmaceuticals and related molecules typically assumes a temperature of about 37 degrees Celsius when in a human body, and can assume other temperature values in other contexts, with the molecule having known fractions of potential energy and vibrational energy.

The BFGS algorithm, or a variant thereof, can be applied at each step of energy minimization with termination conditions suited to the selection of parameters for the force field model. For example, for initial refinement 4, termination conditions can include gradient ≤0.1 (Kcal/mol per Angstrom), atomic position change ≤0.001 (Angstrom), and energy change ≤0.1 (Kcal/mol per Angstrom). However, for substantially final refinement 6, termination conditions can include gradient $10^{-3}$, atomic position change ≤$10^{-5}$, and energy change ≤$10^{-5}$ (same units).

More generally, a selected energy minimization technique can be applied at each step of energy minimization, not necessarily the same technique at each step, with termination conditions selected to be suitable for the selected step of energy minimization. A maximum number of iterations or a maximum run-time can also be imposed.

Verification of the Refined Molecular Structure

The method can determine whether the substantially finally refined molecular structure 6 (shown in FIG. 1) agrees with recorded chirality and bond-configuration constraints, where available. If the molecular structure 6 does not agree, it is rejected, and the method restarts with selection of a new initial molecular structure.

The method can also determine whether the substantially finally refined molecular structure 6 (shown in FIG. 1) has less than a threshold value for energy per atom in the substantially final force field model. If the molecular structure 6 has an energy per atom >7.0 (Kcal/mol per atom), it is similarly rejected, and the method is restarted with selection of a new initial molecular structure.

The method can also determine whether the substantially finally refined molecular structure 6 (shown in FIG. 1) has less energy per atom than a previous best recorded molecular structure. If so, the molecular structure 6 replaces the previous best recorded molecular structure. If not, the molecular structure 6 is rejected as being no better than earlier attempts, and the method is restarted with selection of a new initial molecular structure.

While this Application primarily describes techniques in which only a best molecular structure 6 (shown in FIG. 1) is selected for presentation to the next routine for generation of conformational variants, in the context of the invention, there is no particular requirement for any such limitation. For example, the method can alternatively select the best two or three such molecular structures (or more generally, the best n, for a selected number n) for generation of conformational variants. In such cases, the method may maintain a data structure including up to n such molecular structures, and may accept a newly found molecular structure 6 whenever that molecular structure 6 is superior to the worst currently known molecular structure.

Iteration of Initial Construction and Energy Minimization

The steps of "Initial Construction of 3D Atomic Positions", "Energy Minimization Using Refined Force Field Models", and "Verification of the Refined Molecular Structure" can be repeated, thus generating a new conformational candidate in response to the energy minimization criteria. When the method generates a new substantially finally refined molecular structure, it can determine whether the new substantially finally refined molecular structure is sufficiently good to be retained. If it is not sufficiently good to be retained, it is rejected and the method can be same steps can be repeated. If it is sufficiently good to be retained, the method can replace the earlier worst known molecular structure.

For example, the method can be repeated, thus attempting to find a better new molecular structure, until a termination condition is reached, such as whether the method finds a selected number $a_1$ of acceptable new molecular structures (such as $a_1$=6). If no acceptable new molecular structures are found because all new molecular structures have excessive energy per atom, the best (one or more) new molecular structures with accurate chiral centers and double bonds are selected despite excessive energy per atom.

For another example, the termination condition can include whether the method has made at least a minimum selected number $a_2$ of attempts to find acceptable new molecular structures (such as $a_2$=five times the number of atoms in the selected molecule). Other values for the parameters ($a_1$, $a_2$) can be used, with the understanding that larger values of parameters ($a_1$, $a_2$) likely will take a larger amount of run time.

While this Application primarily describes termination conditions including parameters ($a_1$, $a_2$) for number of successful new molecular structures, and number of attempts to find new molecular structures, in the context of the invention, there is no particular requirement for any such limitation. For example, a termination condition can include whether the method has used a selected amount t of run time (such as t=10 seconds). Alternatively, the termination condition can include whether a user halts operation of the method; however, this is unlikely, and the method is not typically interactive and takes typically only 1-2 seconds per molecule except in rare cases. Other and further termination conditions are also possible.

Figure 2:
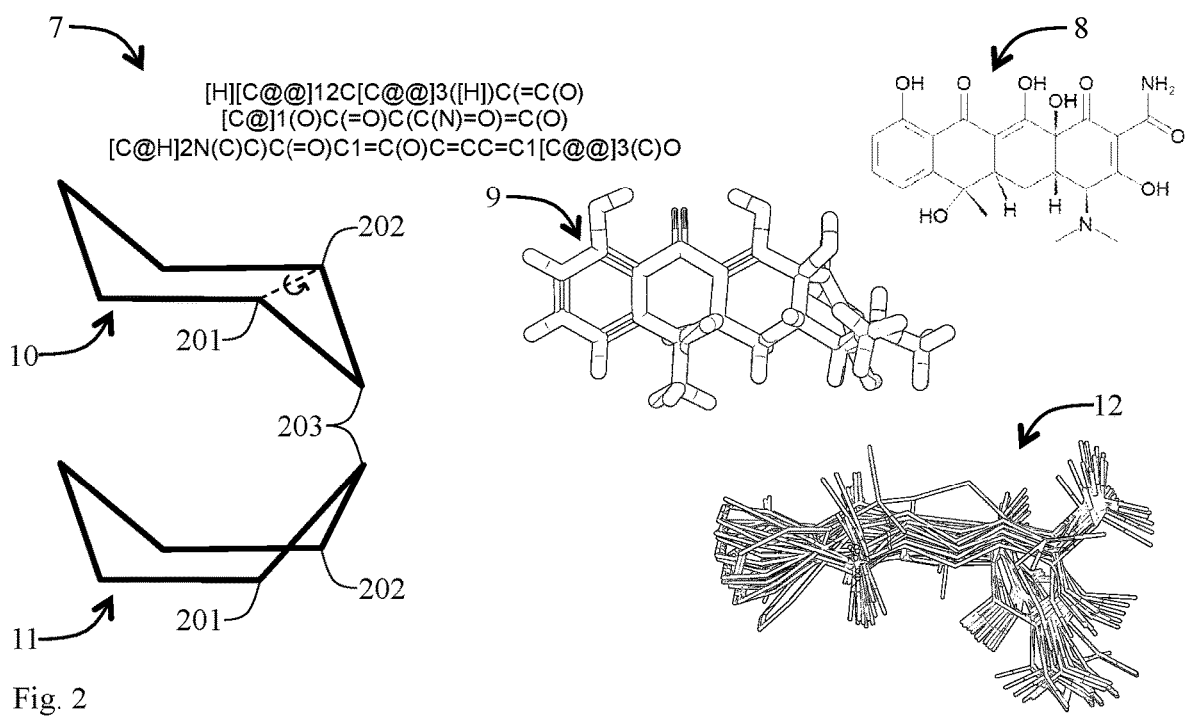
FIG. 2 shows a conceptual drawing of a second example molecular structure, including a linear structure, a 2D structure, possible 3D structures, a selected folding axis across a ring bend, and a set of possible conformational variants.
Figure 3:
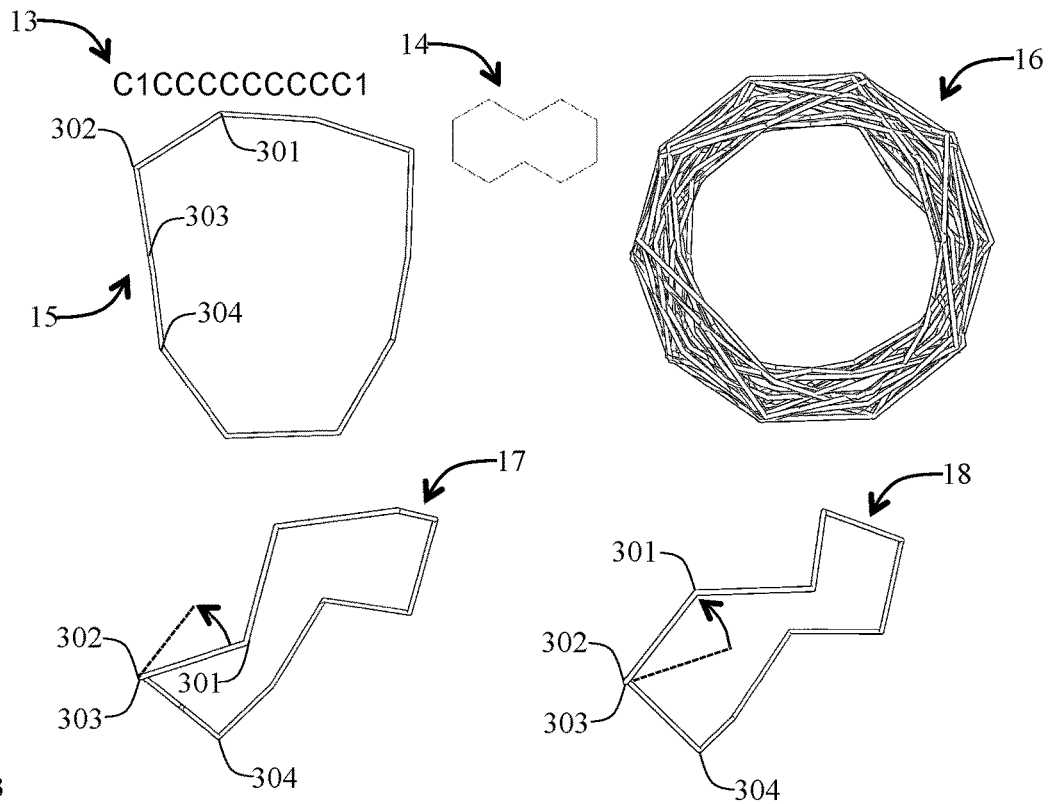
FIG. 3 shows a conceptual drawing of a third example molecular structure, including a linear structure, a 2D structure, a possible 3D macrocyclic structure, a selected rotational axis across a ring twist, and a set of possible conformational variants.

Examples of substantially finally refined molecular structures include molecular structure 6 (shown in FIG. 1), 9 (shown in FIG. 2), and 15 (shown in FIG. 3). The selected one or more molecular structures are presented as a conformational candidate. The method can present the one or more substantially finally refined molecular structures 6, 9, or 15, as first conformational candidates, to a component disposed to generate conformational variants.

While this Application primarily describes operation of the method without use of pre-computed molecular templates, in the context of the invention, there is no requirement for any such limitation. For example, the method can use at least some precomputed molecular templates for well-known substituents of input molecules. In such cases, the well-known substituents may be used as a part of determination of initial molecular structure, with further atomic positioning, energy minimization, and verification being performed to determine first conformational candidates, themselves used to generate conformational variants.

In alternative embodiments, the method can iterate the procedure of producing a conformational candidate. When conformational candidates are nearly identical (such as, <0.1 Angstrom root-mean-squared deviation, or RMSD), they can be discarded as superfluous. When conformational candidates are not superfluous, the conformational candidate with the lowest internal energy according to the modeling force field, as described herein, is selected as the choice conformational candidate, from which the method generates conformational variants.

Generation of Conformational Variants

After producing a conformational candidate, the method performs one or more biophysical transformations on the molecular structure, to produce one or more conformational variants. These biophysical transformations can include ring bends, performed on small ring systems (having rings of size three to eight atoms) or on macrocyclic ring systems (having rings of size nine or more atoms).

For example, ring bend transformations can be performed for all available ring bends, producing an ensemble of conformational variants for small ring systems. For another example, ring twist transformations can be performed for all available ring twists, producing an ensemble of conformational variants for macrocyclic ring systems. For another example, in macrocyclic systems that incorporate small ring systems, a combination of transformations for all available ring bends and ring twists can be performed.

Biophysical Transformations

Biophysical transformations can be performed for one or more ring systems of the conformational candidate. Ring systems can include small ring systems, which include rings of size three to eight atoms, and macrocyclic ring systems, which include rings of size nine or more atoms, and may include components that themselves are small ring systems.

Ring Bends

FIG. 2 shows a conceptual drawing of a second example molecular structure, including a linear structure, a 2D structure, possible 3D structures, a selected folding axis across a ring bend, and a set of possible conformational variants. This example molecular structure is tetracycline. FIG. 2 shows the description of tetracycline in a SMILES string notation 7. FIG. 2 also shows a 2D rendering 8 of the molecule, as an optional second description or representation.

The method can identify one or more ring bends in a small ring system of a molecular structure 9 (shown in FIG. 2). For example, a ring bend can include a pair of atoms having the following properties: (1) the atoms in the ring bend are not directly bonded, (2) at least one of the atoms in the ring bend is part of a non-planar ring, (3) the atoms in the ring bend do not cross a bridged ring atom or a ring fusion.

For example, in FIG. 2, the two atoms 201, 202 are a pair of atoms defining a ring bend, where the third atom 203 is an atom to be adjusted when "bending" the ring bend, thus making a biophysical transformation to the ring system. If the two atoms 201, 202 were themselves also directly bonded, the two atoms 201, 202 would not define a ring bend. As shown in the figure, the ring bend can be transformed by physical bending, shown by moving the atom 203 from a "chair" configuration 10 to a "boat" configuration 11, or vice versa.

The method can identify a left-hand side (LHS) and right-hand side (RHS) of the ring bend. Each side of the ring bend is associated with one side of the ring system relative to an axis between the pair of atoms (such as 201, 202) defining the ring bend. Without loss of generality, the smaller side is labeled the RHS, thus generally including the central atom 203. The method can also note the pendant substituents of the LHS and RHS of the ring bend. For example, the central atom 203 on the RHS might be coupled to a pendant substituent.

To perform the ring bend biophysical transformation, the method first determines a centroid of the LHS and a centroid of the RHS of the ring bend. The then alters the molecular structure by adjusting the angle between the LHS, the axis defined by the ring pair, and the RHS. For example, the method can move the RHS of the ring bend from below the plane of the LHS to above the plane of the LHS, or vice versa. In such cases, the angle is typically adjusted to move the ring bend to the same angle below the plane as it was previously above the plane, and vice versa. Thus, if the angle was 20 degrees above the plane, performing the biophysical transformation on the ring bend will move the angle to 20 degrees below the plane. As described herein, when the method adjusts the angle by moving the RHS of the ring bend, the atoms 201, 202 defining the ring bend and the LHS of the ring bend (or its pendent substituents) need be moved.

The method can then relax the molecular structure about the bend, while maintaining the ring bend in place. For example, the method can "pin" the atoms of the ring bend by applying a quadratic penalty to changes in their positions, and perform energy minimization of the rest of the molecular structure with respect to the force field model (possibly using a relatively more lenient termination cutoff for the BFGS algorithm). For example, the quadratic penalty can include a force of 100.0 Kcal/mol per squared Angstrom, with the effect that a deviation of 0.1 Angstrom would incur a penalty of 1.0 Kcal/mol.

After relaxation with the "pin" is performed, the method can remove the pin and perform a second energy minimization with the pin removed, with a relatively more strict termination cutoff for the BFGS algorithm. This can have the effect of producing sensible variations of small ring systems, while substantially preventing reversion to the original ring conformation unless the new one is inappropriate.

The method can perform a ring bend for each possible ring bend, until all biophysical transformations of ring bends have been attempted on the candidate structure. These bends can give rise to non-redundant ring conformational variants of relatively low energy. The method can repeat the ring bending procedure upon each of the new ring conformational variants, possibly giving rise to yet more non-redundant variants. The method can repeat the process for a specific number of iterations, such as six, or until an earlier termination condition is reached. Earlier termination can occur when an iteration of ring bending yields no new variants, or when a selected maximum amount of computation or a selected maximum amount of run time is used, or another condition.

For example, in FIG. 2, with respect to tetracycline, the method has identified four six-atom ring systems that are completely fused together. When the method performs repeated biophysical transformations on ring bends, it has identified fifteen distinct conformational variants within 10.0 Kcal/mol of the lowest energy conformational variant. These biophysical transformations do not require any pre-computation of conformational variants or other molecular structures. Moreover, performing biophysical transformations is fully general, and applicable to molecular structures both known and unknown.

The inventor has found that for relatively simple small ring systems, such as cyclohexane, finding conformational variants can take on the order of about one-tenth of a second (on an ordinary contemporary laptop computer, without special hardware acceleration). For more complex ring systems, timing can depend on the relative rigidity of the molecular structure. For example, steroids such as testosterone can take about a few seconds, while more flexible molecular structures such as tetracycline can take a few tens of seconds.

Ring Twists

FIG. 3 shows a conceptual drawing of a third example molecular structure, including a linear structure, a 2D structure, a possible 3D macrocyclic structure, a selected rotational axis around a ring twist, and a set of possible conformational variants. This example molecular structure is cyclic decane. FIG. 3 shows the description of cyclic decane in a SMILES string notation 11. FIG. 3 also shows a 2D rendering 14 of the molecule, as an optional second description or representation.

A ring twist can include any single atomic bond in a macrocyclic ring system, such as the bond between atoms 302, 303 in the molecular structure 15 (shown in FIG. 3), along with the adjacent atomic bonds, such as the bonds between atoms 301, 302 and between atoms 303, 304. As shown in the figure, the ring twist thus includes three atomic bonds 301-302, 302-303, and 303-304, with the central atomic bond being between atoms 302, 303.

The method can pin the atoms in the ring twist by applying a quadratic penalty to changes in their positions, similar to the quadratic penalty used for ring bends. For example, the quadratic penalty can include a force of 100.0 Kcal/mol per squared Angstrom, with the effect that a deviation of 0.1 Angstrom would incur a penalty of 1.0 Kcal/mol. For ring twists, the method can allow the three atoms 301, 302, 303 in the ring twist freedom to move up to 0.1 Angstrom without incurring the quadratic penalty. Thus, the quadratic penalty is only quadratic in shape after the initial amount of freedom (that is, it has a square bottom before becoming quadratic). This can have the effect of accommodating constraints of maintaining physical ring-closure, while still allowing the fourth atom 304 to rotate about the central bond 302-303.

The method can alter the molecular structure by adjusting the angle between the center bond 302-303 of the ring twist and a side bond of the ring twist, such as 303-304. The method can alter the angle of the side bond 303-304 with respect to the center bond 302-303 by moving the atom 304 relative to the center bond 302-303. For example, the method can rotate the atom 304 about an axis defined by the center bond 302-303, by an angle of 60, 120, 180, or 240 degrees, or by other amounts. In such cases, for each rotation angle amount, the other three atoms 301, 302, 303 are pinned in their original positions, and the fourth atom 304 is pushed into its desired rotated position by imposing a quadratic penalty for deviation from the desired position. The method can perform ring twists by moving the atom 304 in either rotational direction. In such cases, performing a biophysical transformation on the ring twist can alter a known conformational variant 17 (a bottom view shown in the figure) to a newly found conformational variant 18.

The method can perform a first energy minimization with respect the force field while the atoms involved in the ring twist are pinned. Although energy minimization using the complete force field definition is primarily described, the method can (optionally) use only a limited set of parameters for the force field. After the first energy minimization, the method can release the pin and re-perform energy minimization with respect the force field, using the complete set of force field terms. Similar to the pin and energy minimization steps performed with respect to ring bends, the energy minimization with the pin in place can be performed with a relatively more lenient cutoff for the BFGS algorithm, while the energy minimization with the pin released can be performed with a relatively more strict cutoff for the BFGS algorithm. This can have the effect of generating relatively low-energy conformational variations of macrocyclic systems, while overcoming some high-energy barriers between relative energy minima.

The method can perform the ring twist for the bond on the other side of the central bond 302-303. Thus, the method can alter either one side of the ring twist, by moving atom 301, or the other side of the ring twist, by moving atom 304. For example, the method can perform ring twists with respect to one side, collect conformational variants, and then perform ring twists with respect to one side on those conformational variants.

The method performs each possible ring twist on the candidate structure. These twists can give rise to non-redundant ring conformational variants of relatively low energy. The method can repeat the ring twisting procedure upon each of the new ring conformational variants, possibly giving rise to yet more non-redundant variants. The method can repeat the process for a specific number of iterations, such as six, or until an earlier termination condition is reached. Earlier termination can occur when an iteration of ring twisting yields no new variants, or when a selected maximum amount of computation or a selected maximum amount of run time is used, or another condition.

For example, in FIG. 3, with respect to cyclic decane, the method has identified a set of conformational variants 16, one of which is within 0.01 Angstroms RMSD of matching experimental measurements. When the method performs repeated biophysical transformations on ring twists, it can attempt to generate distinct conformational variants that are each within 20.0 Kcal/mol of the lowest energy conformational variant found so far.

Similar to ring bends, these biophysical transformations on ring twists do not require any pre-computation of conformational variants or other molecular structures. Moreover, also similar to ring bends, performing biophysical transformations on ring twists is fully general, and applicable to molecular structures both known and unknown.

Other Biophysical Transformations

While this Application primarily describes biophysical transformations on ring bends for small ring systems, and on ring twists for macrocyclic ring systems, in the context of the invention, there is no particular requirement for any such limitation. For example, biophysical transformations on ring bends can be performed for ring systems other than the limited set of small ring systems described herein, and biophysical transformations on ring twists can be performed for ring systems other than the limited set of macrocyclic ring systems described herein. For another example, identification of a pair of bonds within a macrocycle can be used to perform a "flip" of the atoms and substituents between the two bonds, such as by rotating an entire substructure of the molecule found between two bonds that are otherwise held constant. For another example, identification of pairs of complementary hydrogen bonding atoms within a macrocycle can be used to force the bridging of a macrocyclic ring by one or more hydrogen bonds.

Biophysical transformations are distinct from torsional adjustments made at places in the molecular structure where substituents are otherwise free floating. Thus, biophysical transformations include adjustments to molecular structure distinct from, for example, twisting the central bond in 1,2-dichloroethane. While this Application primarily describes adjustments to molecular structure other than torsional adjustments, in the context of the invention, it is of course also possible to also adjust molecular structure to generate conformational variants using torsional adjustments.

The method can also perform torsional sampling on atomic bonds, such as described in the Technical Appendix. For example, the method can perform torsional sampling including a selected sampling density, and can be performed iteratively for bond groups with compression between iteration steps. For another example, the method can perform torsional sampling including a non-exhaustive sampling procedure. The method can also perform torsional sampling in combination with one or more biophysical transformations, or with one or more types of biophysical transformations.

Verification of Conformational Variants

The method can verify each new conformational variant that was generated by a biophysical transformation. In one embodiment, the method can determine whether the new conformational variant is consistent with physical constraints, has not inverted any configuration requirements (such as changing the chirality at a specified center), and whether the new conformational variant satisfies the minimum-energy and nonredundancy requirements described herein.

Compression of Conformational Variants

Sufficient Distinctiveness

The method can maintain a pool of conformational variants, adding each newly found conformational variant to the pool as it is collected. As each conformational variant is newly found, the method can determine whether that conformational variant is sufficiently distinct from other conformational variants. The method can compare each newly found conformational variant with each other conformational variant in the pool, to determine a root mean square difference (RMSD), and can reject newly found conformational variants that are not sufficiently distinct from all other conformational variants to the pool. For example, if a newly found conformational variant has an RMSD of less than a selected threshold d (such as d=0.1 Angstrom) from some conformational variant already in the pool, the method can reject that newly found conformational variant.

For another example, the RMSD threshold can be selected in response to a molecular structure. In such cases, the selected threshold d can be set to 0.1 Angstrom for systems with fewer than 10 atoms, 0.2 Angstrom for systems with less than 35 atoms, 0.3 Angstrom for larger ring systems, and 0.5 Angstrom for macrocyclic ring systems in which the entire molecular structure contributes to the RMSD difference value.

Maximum Energy Threshold

The method can verify each newly found conformational variant as it is found, to determine whether each new conformational variant is within a maximum energy threshold $t_E$ (such as $t_E=20.0$ Kcal/mol) of the lowest known conformational variant maintained in the pool. When the pool of known conformational variants is maintained sorted by minimum energy, this verification need include checking each newly found conformational variant against only O(1) known conformational variants in the pool.

The method can select the maximum energy threshold $t_E$ in response to a stage at which the method is collecting conformational variants. For example, the method can select a first maximum energy threshold $t_{ES}$ while collecting conformational variants for small ring systems and a second maximum energy threshold $t_{EM}$ while collecting conformational variants for macrocyclic ring systems. For another example, the method can select a maximum energy threshold $t_E$ that varies (up or down) in response to a number of conformational variants found so far.

Instead of performing a separate verification for each new conformational variant, the method can perform verification for groups of conformational variants. For example, the method can determine, for each small ring system or macrocyclic ring system, whether each new conformational variant is a lower-energy alternative. In such cases, the method can replace the original conformational variant for that ring system, and repeat the routine of generating conformational variants for that ring system. The method can continue repeating generating conformational variants for that ring system until a selected number of iterations r have been completed (such as r=6) or until no further conformational variants are found.

Presentation of Conformational Variants

The method can select one or more of the conformational variants for presentation. For example, the method can present all of the conformational variants in the pool. Presentation can be to a user; to another computer application, subsystem, or system; or to a database for later use with another computer application, subsystem, or system.

Results

Figure 4:
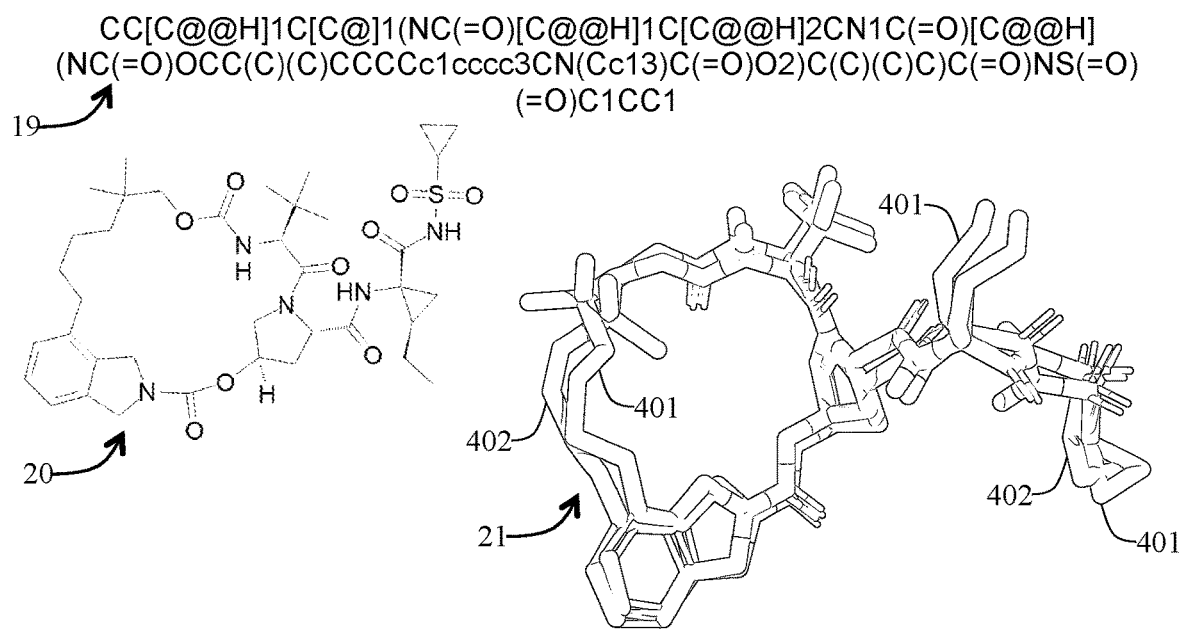
FIG. 4 shows a conceptual drawing of a fourth example molecular structure, including a linear structure, a 2D structure, and a possible 3D structure including after conformational exploration superimposed upon the experimentally determined conformation when bound to the biologically relevant enzyme.

FIG. 4 shows a conceptual drawing of a fourth example molecular structure, including a linear structure, a 2D structure, and a possible 3D structure including after conformational exploration. This example molecular structure is the drug vaniprevir. FIG. 4 shows the description of vaniprevir in a SMILES string notation 19. FIG. 4 also shows a 2D rendering 20 of the molecule, as an optional second description or representation.

After a 3D molecular structure is generated and conformational variants are determined, the method finds a low-energy conformational variant 402 that is a very close match to the bioactive conformer 401 when bound to the drug's therapeutic target HCV NS3/4a protease. The bioactive conformer 401 and the discovered conformational variant 402 differ by less than 1.0 Angstrom RMSD.

The inventor has found that the techniques described herein are extremely general. For example, these techniques can generate an ensemble of low-energy conformational variants in response to a molecular structure, using natural movements that are not limited by high-energy intermediate states that the known art (such as methods that use molecular-dynamics simulation) cannot easily overcome. Moreover, the techniques described herein generally involve only a molecular force field and a description of molecular structure (such as atomic composition, bond connectivity, chirality, and configurations of double-bonded carbons). They do not need pre-computation of ring structural variations or other atomic sub-structural components.

Alternative Embodiments

While this Application sometimes describes techniques related to determining molecular structures (and conformational variants thereof) for molecules related to human therapeutics, in the context of the invention, there is no particular reason for any such limitation. Techniques described herein have broad applicability to other molecules related to human biochemical processes, whether conducted in the body or in a laboratory context (such as for assays), or molecules related to animal biochemical processes, or molecules related to use with respect to herbicides or pesticides, or molecules related to testing (such as testing for toxicity), or molecules related to other human conduct.

After reading this Application, those skilled in the art would recognize other and further uses for performing biophysical transformations on molecular structures, other and further techniques (including systems and methods) for conducting those biophysical transformations. The claims and Technical Appendix are hereby incorporated into this specification as if fully set forth herein.

The invention claimed is:

1. A method for generating conformational variations of three-dimensional (3D) molecular structures of organic molecules, the method including steps of
receiving one or more representations of a selected molecule, said representations identifying assignment of 3D atomic positions and atomic bonds;
identifying one or more ring systems in the selected molecule;
performing one or more biophysical transformations on the ring systems, said biophysical transformations representing natural physical adjustment of one or more of the atomic positions with respect to a geometric or topological feature of the selected molecule;
selecting one or more conformational variants in response to a measure of molecular energy; and
repeating the steps of performing, producing, and selecting until a termination condition is reached;
wherein the steps of selection of conformational variants are responsive in multiple stages to an energy window above a selected currently known minimum energy conformational variant, with the energy window having larger windows than later stages, and with the energy window for a final stage being responsive to a specified parameter; and
wherein the steps of selection of conformational variants are responsive to a maximum number of individual conformers.

2. A method as in claim 1,
including steps of
torsional sampling for rotatable bonds outside of ring systems;
selection of diverse conformational variants; or
energy minimization with respect to a force field.

3. A method as in claim 1,
wherein the terminating condition includes one or more of:
a maximum number of conformational variants are identified, the maximum number of conformational variants being responsive to one or more of: a number of rotatable bonds in the molecule, a user specification;
a maximum number of attempts to identify conformational variants are made;
a maximum amount of computation or run time is used.

4. A method as in claim 1,
wherein the steps of selecting are responsive to one or more of:
a measure of differences between conformational variants,
an evaluation of configurational correctness.

5. A method for generating conformational variations of three-dimensional (3D) molecular structures of organic molecules, the method including steps of
receiving one or more representations of a selected molecule, said representations identifying assignment of 3D atomic positions and atomic bonds;
identifying one or more ring systems in the selected molecule;
performing one or more biophysical transformations on the ring systems, said biophysical transformations representing natural physical adjustment of one or more of the atomic positions with respect to a geometric or topological feature of the selected molecule;
selecting one or more conformational variants in response to a measure of molecular energy; and
repeating the steps of performing, producing, and selecting until a termination condition is reached;
wherein the steps of selecting are responsive to
eliminating redundant conformational variants from ring system elaboration in response to thresholds on RMS deviation that depend on ring system size or upon user specification;
eliminating redundant conformational variants from torsional elaboration in response to thresholds on RMS deviation that depend upon user specification; or
compression of conformational pools in response to selection of maximally different conformational variants.

6. A method as in claim 5,
including steps of
torsional sampling for rotatable bonds outside of ring systems;
selection of diverse conformational variants; and
energy minimization with respect to a force field.

7. A method as in claim 5,
wherein the terminating condition includes one or more of:
a maximum number of conformational variants are identified, the maximum number of conformational variants being responsive to one or more of: a number of rotatable bonds in the molecule, a user specification;
a maximum number of attempts to identify conformational variants are made;
a maximum amount of computation or run time is used.

8. A method for generating conformational variations of three-dimensional (3D) molecular structures of organic molecules, the method including steps of
receiving one or more representations of a selected molecule, said representations identifying assignment of 3D atomic positions and atomic bonds;
identifying one or more ring systems in the selected molecule;
performing one or more biophysical transformations on the ring systems, said biophysical transformations representing natural physical adjustment of one or more of the atomic positions with respect to a geometric or topological feature of the selected molecule;
selecting one or more conformational variants in response to a measure of molecular energy; and
repeating the steps of performing, producing, and selecting until a termination condition is reached;
wherein the ring systems include at least one macrocyclic structure having a connected ring structure of size nine or more,
wherein the macrocyclic structure includes a torsional group of four atoms, the central two having a bond defining a twisting axis, a third atom defining an anchor, and a fourth atom defining a twistable atom;
wherein the biophysical transformation includes a ring twist, the ring twist including rotating the twistable atom relative to the twisting axis, while the anchor atom maintains its position relative to the twisting axis;
wherein the biophysical transformation includes performing the ring twist and conducting energy minimization with respect to a force field.

9. A method as in claim 8,
wherein pinning the ring twist is of sufficient magnitude to prevent reversion or lack of sampling.

10. A method as in claim 8,
wherein pinning the ring twist includes a square-welled quadratic penalty associated with a freedom of movement for the three atoms being held as fixed.

11. A method as in claim 8,
wherein ring twists include increments of regular increments, including 180 degrees and a rotation beyond 180 degrees.

12. A method as in claim 8,
wherein the steps of conducting energy minimization with respect to a force field
include steps of
conducting energy minimization while pinning the anchor atom, the twistable bond, and the twistable atom;
relaxing the pin; and
conducting energy minimization without pinning the anchor atom, the twistable bond, and the twistable atom.

13. A method as in claim 8,
wherein the steps of performing the ring twist are performed for each ring twist in the macrocyclic structure.

14. A method as in claim 8,
wherein the steps of performing the ring twist are performed for more than one amount of rotation about the twistable bond.

15. A method as in claim 8,
including steps of
torsional sampling for rotatable bonds outside of ring systems;
selection of diverse conformational variants; and
energy minimization with respect to a force field.

16. A method as in claim 8,
wherein the terminating condition includes one or more of:
a maximum number of conformational variants are identified, the maximum number of conformational variants being responsive to one or more of: a number of rotatable bonds in the molecule, a user specification;
a maximum number of attempts to identify conformational variants are made;
a maximum amount of computation or run time is used.

17. A method for generating three-dimensional (3D) molecular structures for conformational candidates of organic molecules, the method including steps of assigning initial atomic coordinates in response to molecular connectivity;

refining those coordinates to minimize molecular energy while adhering to constraints upon molecular configuration;

selecting candidate molecular structures in response to a measure of molecular energy and an assessment of congruence with specified molecular configuration; and repeating the steps of assigning initial atomic coordinates, refining those coordinates, and selecting candidate molecular structures, until a termination condition is reached;

wherein the steps of assigning initial atomic coordinates include steps of computing initial approximate atomic positions by modeling each atom as a tetrahedron and by using approximate bond lengths and torsional choices to avoid energetically unfavorable configurations;

wherein the steps of refining those coordinates include steps of assigning initial equal atomic partial charges, refining the initial positions using force field minimization including force field terms that include bond length, bond angle, and electrostatic terms, imposing force field terms to enforce specified chirality at tetrahedral centers, followed by energy minimization, imposing force field terms to enforce specified double-bond configurations along with all torsional terms, followed by energy minimization, and removing special configurational force field terms, assigning partial charges using a standard method, and minimizing the energy using all standard force field terms;

repeating the preceding steps with alternative initial atomic coordinate assignments; and wherein the steps of selecting candidate molecular structures include steps of collecting the conformational variants so generated and evaluating each for configurational correctness and satisfaction of a maximum energy cutoff, terminating the repetition of steps when a fixed number of conformers meet the evaluation criteria or when a maximal number of repetitions has occurred, and producing the atomic coordinates of the conformer with lowest energy that passed the configurational correctness criteria.

18. A method as in claim 17,
including steps of
torsional sampling for rotatable bonds outside of ring systems;
selection of diverse conformational variants; and
energy minimization with respect to a force field.

* * * * *